United States Patent [19]
Drobish et al.

[11] 4,219,016
[45] Aug. 26, 1980

[54] VAGINAL CONTRACEPTIVE

[75] Inventors: James L. Drobish; Thomas W. Gougeon, both of Cincinnati, Ohio

[73] Assignee: The Procter & Gamble Company, Cincinnati, Ohio

[21] Appl. No.: 967,195

[22] Filed: Dec. 7, 1978

Related U.S. Application Data

[63] Continuation of Ser. No. 748,267, Dec. 7, 1976, abandoned.

[51] Int. Cl.³ .............................................. A61F 5/46
[52] U.S. Cl. ............................................ 128/130
[58] Field of Search ....................... 128/127–130, 128/260–261, 268, DIG. 21

[56] References Cited

U.S. PATENT DOCUMENTS

| | | | |
|---|---|---|---|
| 2,697,057 | 12/1954 | Senger et al. | 128/127 |
| 3,015,598 | 1/1962 | Jones | 128/127 |
| 3,216,422 | 11/1965 | Steiger et al. | 128/127 |
| 3,279,996 | 10/1966 | Long, Jr. et al. | 128/DIG. 21 |
| 3,971,367 | 7/1976 | Zaffaroni | 128/260 |
| 3,991,760 | 11/1976 | Drobish et al. | 128/260 |
| 3,993,073 | 11/1976 | Zaffaroni | 128/260 |
| 3,995,633 | 12/1976 | Gougeon | 128/127 |
| 3,995,634 | 12/1976 | Drobish | 128/260 |
| 4,012,497 | 3/1977 | Schopflin | 128/260 |
| 4,016,251 | 4/1977 | Higuchi et al. | 128/260 |
| 4,031,202 | 6/1977 | Laughlin et al. | 128/260 |
| 4,067,961 | 1/1978 | Laughlin | 128/260 |
| 4,073,833 | 2/1978 | Laughlin | 128/130 |

FOREIGN PATENT DOCUMENTS 21588 of 1896 United Kingdom ................. 128/127

OTHER PUBLICATIONS

Wo 79/00014, Biologically Compatible Tampon Sponge, Jan. 1, 1979, priority 6-77, Vorhauer et al.

Primary Examiner—C. Fred Rosenbaum
Attorney, Agent, or Firm—Jerry J. Yetter; Michael J. Roth; Richard C. Witte

[57] ABSTRACT

Improved devices which can be retained in the vagina during intercourse deliver spermicidal surfactants and provide contraceptive benefits.

27 Claims, 3 Drawing Figures

U.S. Patent     Aug. 26, 1980     4,219,016
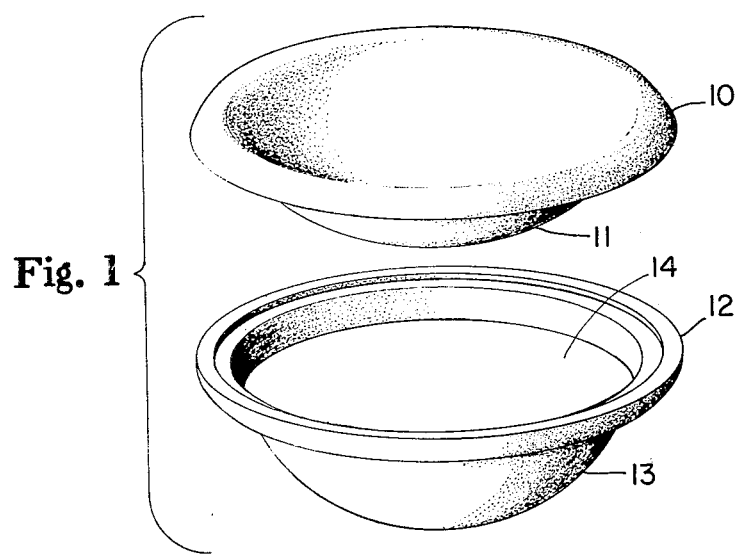
Fig. 1
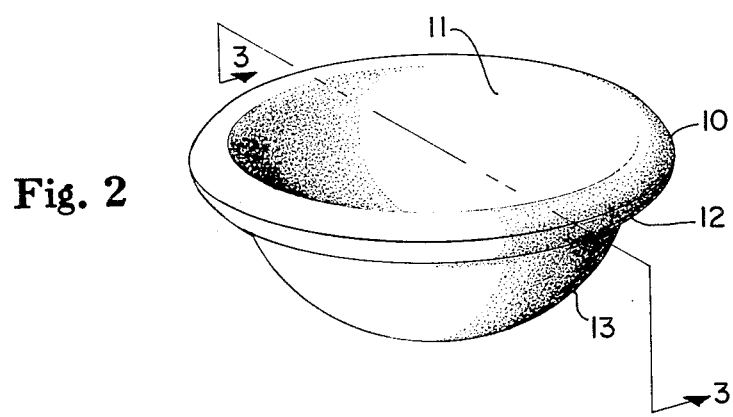
Fig. 2
Fig. 3
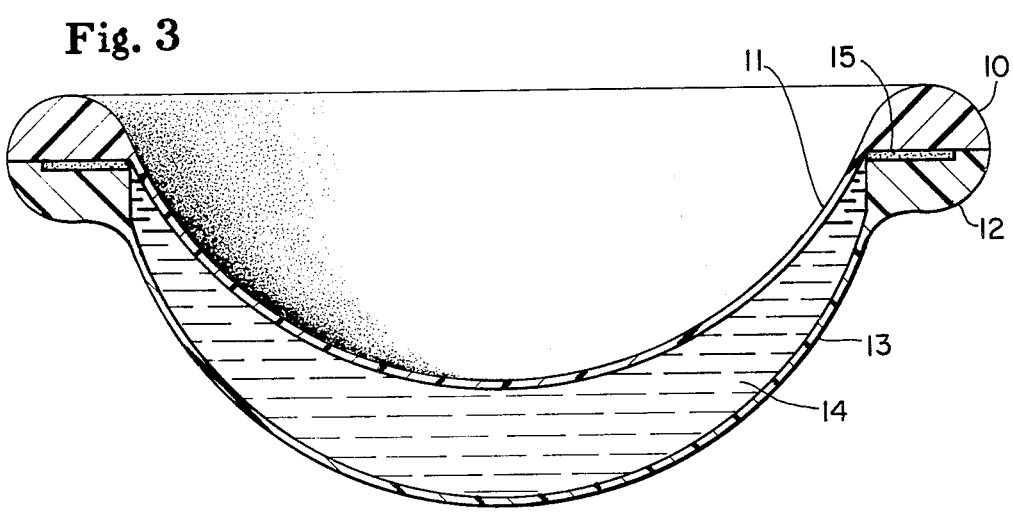

VAGINAL CONTRACEPTIVE

This is a continuation of application Ser. No. 748,267, filed Dec. 7, 1976, now abandoned.

BACKGROUND OF THE INVENTION

The present invention encompasses devices which are used in the vagina to deliver spermicidal surfactants. By virtue of their unique construction and shape, the devices remain in position, even during intercourse, so that delivery of the spermicidal surfactant is not interrupted.

The devices of this invention are designed for use in the vagina, can be inserted by the user, and do not require insertion by a physician as, for example, in the case of intrauterine contraceptive devices. The devices are designed to remain in the vagina during the time between menstrual periods to provide desirable, prolonged release of a spermicidal surfactant, and their construction and shape facilitate retention therein. An effective between-period contraceptive device is thereby provided.

SUMMARY OF THE INVENTION

The present invention combines the desirable features of devices which provide prolonged release of medicaments, e.g., spermicides, or the like, into the vaginal area with the added advantages that the unique construction and shape of the present devices allows them to be worn comfortably in the vagina for periods of several weeks and to remain substantially undisturbed within the vaginal cavity during sexual intercourse.

Most importantly, the construction of the present devices allows them to be positioned in the vagina in such a way that maximum contraceptive protection is secured. As can be seen by reference to the Figures herein, the highly preferred devices of the present type for use within the vaginal cavity are characterized by a dome-shaped construction and comprise one or more containers, said containers having walls which allow passage of spermicidal surfactant monomers from within the containers into the vagina. The configuration of the devices allows them to be placed in the closest possible proximity to the cervical os, and this feature contributes importantly to their contraceptive efficacy. Indeed, the highly preferred dome-shaped devices herein substantially surround and "cap" the cervical os.

The contraceptive devices of this invention make use of the association colloid nature of solutions of certain spermicidal surfactants to provide a reservoir from which spermicide is released in a controlled manner through the semi-permeable membrane which comprises at least a portion of the wall of the container. Surfactant micelles, as is, cannot diffuse through the semi-permeable membrane; they must first dissociate, at or remote from the membrane, to individual surfactant molecules which then dissolve in the membrane material and diffuse therethrough to its outer surface, whereupon the surfactant monomers are free to dissolve in the surrounding vaginal fluid to provide their contraceptive effect. Since the predominant driving force for diffusion is the concentration difference between unassociated (i.e., monomeric) surfactant molecules in the solution inside and outside the contraceptive device, the rate of transport will slow drastically when the exterior surfactant monomer concentration approaches that on the interior of the device, thus producing a desirable controlled release behavior of the surfactant through the membrane. In the present devices, the bulk of the surfactant remains in micellar form, where it resides in reserve to provide a source of monomers over a long period of time, thereby delivering continuous contraceptive protection to the user for a time period of 20–30 days.

As will be seen from the following disclosure, the present invention encompasses contraceptive devices which are especially adapted for use within the vaginal cavity at a position posterior to the introitus and in close proximity to the cervical os, characterized by: vaginal retaining means having affixed thereto one or more containers having walls, at least a portion of the walls comprising a substantially non-porous, semi-permeable membrane, said containers holding a reservoir of spermicide comprising an aqueous solution of a micelle-forming spermicidal surfactant compound at a concentration at or above the critical micelle concentration of said surfactant compound, said membrane-walled containers being maintained in position in the device by positioning means, thereby providing a transport surface on the face of the device. Preferred devices are those wherein the transport surface extends substantially across the face of the device. Domed or "cup-shaped" devices which can be positioned to substantially cap the cervical os are an especially preferred embodiment of the invention.

Devices according to this invention wherein the container walls which face the cervical os comprise the substantially non-porous, semi-permeable membrane transport surface are preferred, inasmuch as the spermicidal surfactant is thereby delivered directly to its prime situs of action. Moreover, delivery of excess surfactant to the general vaginal cavity is thereby avoided. However, devices wherein all container walls comprise the substantially non-porous, semi-permeable membrane transport surface are also useful and are encompassed by this invention.

The most highly preferred embodiment of the present contraceptive device comprises; a double-walled, dome-shaped disc suitable for capping the cervical os, at least one wall of said disc comprising a non-porous, semi-permeable membrane having a thickness in the range of from about 0.1 mm to about 0.4 mm, said walls being sealed together to provide containers, said containers holding an aqueous solution comprising from about 10% to about 50% by weight of $C_{10}EO_5$ or $C_{10}EO_6$. Such devices wherein the walls are sealed together around their peripheral edges to provide a container with a dimensionally-stable rim as the retaining means, and especially those devices wherein only the transport surface facing the cervical os comprises the semi-permeable membrane, are especially useful and preferred herein.

Another preferred embodiment comprises a double-walled, dome-shaped device wherein the outer dome-shaped wall comprises a dimensionally-stable, non-permeable retaining means and wherein the inner wall (facing the cervical os) comprises the non-porous, semi-permeable membrand transport surface.

This invention also provides a method for achieving contraception in the vagina, comprising: inserting within the vaginal cavity at a position posterior to the introitus and in close proximity to the cervical os a device characterized by: vaginal retaining means having affixed thereto one or more containers having walls, at least a portion of the walls comprising a substantially non-porous, semi-permeable membrane, said containers holding a reservoir of spermicide comprising an aqueous solution of a micelle-forming spermicidal surfactant compound at a concentration at or about the critical micelle concentration of said surfactant compound, said membrane-walled containers being maintained in position in the device by positioning means, thereby providing a transport surface on the device, and placing the device so that the transport surface substantially covers or "blocks" the cervical os, whereby surfactant monomers diffuse from the device through the membrane transport surface and substantially bathe the cervical os with surfactant in the vaginal fluids to provide a spermicidal effect on sperm coming in contact therewith.

The devices herein are prepared from components which are described in detail hereinafter.

BRIEF DESCRIPTION OF THE DRAWINGS

FIG. 1 is an exploded plan view;
FIG. 2 is an assembled plan view; and
FIG. 3 is a sectional view taken along line 3—3 of FIG. 2.

DESCRIPTION OF THE INVENTION

FIG. 1 is an exploded view of the highly preferred dome-shaped device of the present type. The device comprises two dome-shaped discs which are assembled into a "double-domed" structure.

As seen from FIG. 1, the first, or inner, disc comprises a membrane 11 which is permeable to surfactant monomers but which is not permeable to the passage of surfactant micelles therethrough, and a seal rim 10. conveniently, seal rim 10 is fashioned from the same material used to prepare semi-permeable membrane 11 during the molding process.

The second, or outer, dome-shaped half of the preferred device comprises a toxicologically-acceptable material 13 and a seal rim 12. The toxicologically-acceptable material used to fashion the dome on this portion of the article need not be a semi-permeable membrane material.

FIG. 1 depicts the halves of the device in proper juxtaposition for assembling. To assemble the device, the seal rims can be heat-sealed or sealed by an adhesive, thereby leading to the assembled device depicted in FIG. 2.

FIG. 3 is a section view of the assembled dome-shaped device showing the relationship of the semi-permeable membrane 11, the outer dome material 13, seal rims 10 and 12 sealed with an adhesive 15. The container formed by joining the two halves of the device is substantially filled with an aqueous solution of spermicidal surfactant 14. In use, the dome-shaped device is inserted into the vagina posterior to the introitus to substantially "cap" the certival os such that semi-permeable membrane 11 is in the closest possible proximity to the os.

It will be appreciated that other configurations for the present devices can be used, if desired, to provide vaginal contraceptives. Devices of such alternate configurations are also encompassed by this invention.

For example, the devices herein can be in the configuration of a flat, rather than dome-shaped, disc. The walls of the flattened disc are assembled to provide a container for the surfactant solution. At least one wall of the container is made from a membrane material of the type disclosed hereinafter which will allow passage of surfactant monomers therethrough, but which substantially retains surfactant micelles and water within the container. In use, such a device is positioned with the semi-permeable membrane facing the cervical os, whereby the os is substantially bathed in spermicidal surfactant as monomers are released through the membrane.

In another, alternate structure, flat or dome-shaped devices are compartmentalized into multiple containers, the walls of said containers comprising the semi-permeable membrane and positioned so that they face the cervical os. Such devices having a plurality of containers offer the advantage that, in case of accidental rupture of some containers in use, other containers remain intact to continue delivering spermicidal surfactant monomers to the area surrounding the cervical os.

As shown in the Figures, seal rim 12 depicted in the preferred, double-domed disc structure provides a positioning means which serves to join the halves of the device and to maintain the membranous container in the proper position to provide a transport surface for the spermicidal surfactant. Moreover, the seal rim is thicker and more resilient than other parts of the device, and thus also provides the vaginal retaining means which holds the device in place within the vagina during use. It will be appreciated that vaginal retaining means other than a seal rim can be employed for these purposes. For example, a disc-shaped device of the type depicted in the Figures can be prepared using a relatively thick, pliable, yet resilient and comfortable outer dome positioning means with a semi-permeable membrane inner dome affixed thereto. The resilience of the outer dome also provides the retaining means. Thus, this single structural member both holds the inner domed membrane in the device, and provides the means whereby the device, itself, is retained in the vagina.

Other alternate configurations for the vaginal retaining means in disc-shaped devices include, for example, tri-lobal discs and multi-lobal discs such as hexa-lobal and octa-lobal discs. In such devices, the rim or edge around their periphery is characterized by a plurality of soft, comfortable, yet resilient lobes which promote retention of the device in the vagina.

By the present invention, devices which deliver metered doses of spermicidal surfactants to the vaginal cavity are constructed to provide a shape or configuration whereby said devices can remain in the vagina during intercourse.

The configuration of the devices herein is designed to provide a semi-permeable membrane as a transport surface for the surfactant monomers, said transport surface extending across the entire surface of the cervix (i.e., substantially covering the cervical os). This eliminates problems occasioned by small lateral movements of the device associated with muscular contractions/exertions of the user during wear. Most importantly, by providing a transport surface which is in the closest possible proximity to the cervix, the surfactant has the shortest possible path to the cervical os. Since conception is associated with transmittal of sperm into the os, it will be appreciated that, by delivering surfactant monomers in the most efficient manner to this point in the vagina, the most efficient and effective contraceptive protection is provided.

The configuration of the present device allows them to be positioned in close proximity to the cervical os (i.e., actually touching or within a distance of ca. 1 mm to 10 mm) or, in the case of the preferred dome-shaped device, substantially enveloping and capping the cervical os. Thus, the present devices deliver the spermicidal surfactants more efficiently and effectivey than the devices disclosed in the new-allowed U.S. Patent applications of Gougeon and Drobish, Ser. Nos. 636,897; 636,898 and 636,899.

The desirability of providing metered dosage forms of various biologically active or medicinal agents has long been recognized. Metered dosages can be manifest either as "controlled release" or "sustained release" of a given material. The distinction between controlled release and sustained or prolonged release has been recognized; see Cowsar, in "Advances in Experimental Medicine and Biology", Vol. 49, "Controlled Release of Biologically Active Agents", Ed. Tanquary and Lacey, Plenum Press, New York 1974.

Briefly stated, controlled release devices of the present type respond rapidly to changes such as dilution effects in the environment external to the article, e.g., by body fluid changes, whereas sustained release articles do not. The net result is that devices based on the principle of controlled release are capable of rapidly establishing an effective level or concentration of a medicament or other agent in a selected environment, and then substantially shutting off release to maintain the concentration at that level. In contrast, sustained release articles dispense an agent at a constant rate and do not display the feedback regulation of release that a controlled release article displays.

It will be appreciated that devices operating by the controlled release mechanism provide substantial advantages over sustained release articles for certain uses. For example, placement of a properly formulated controlled release medicament system in an animal's body cavity in contact with body fluids establishes and maintains an effective concentration of the medicament in the fluids. The system responds to dilution or depletion as additional fluids are secreted, or the medicament is bound to tissue, absorbed, etc., thereby automatically maintaining the concentration of medicament at the proper level.

As disclosed by Laughlin in German Pat. No. 2.610,880, open to inspection Oct. 7, 1976, solutions of micelle-forming surfactant compounds can be releasably enclosed in a container comprising a microporous membrane. Articles thus prepared are stable and do not suffer osmotic rupture when placed in body cavities in contact with body fluids. Rather, the stable articles provide controlled release of the surfactant into the body fluids. The proper selection of membrane and surfactant provides a means for achieving various biological effects, e.g., antimicrobial activity, spermicidal activity, and the like. Laughlin teaches the use of porous membranes such as cellulose. However, cellulose is fragile and is quite difficult to fashion into controlled release devices.

By the present invention, it has been discovered that various non-porous elastomers can be fashioned into membranes which allow passage of spermicidal surfactant monomers therethrough in a controlled manner. Such membranes are not fragile; accordingly, stable controlled release articles with optimal shapes for providing vaginal contraceptive protection are readily made therefrom.

Moreover, the membranes used in the present devices are substantially impervious to liquid water. In use, the monomers of spermicidal surfactant diffuse through the membrane into the vagina (presumably by virtue of their solubility in the membrane), whereas the surfactant micelles do not. Since the membranes are non-porous and are substantially impervious to bulk water and body fluids, they do not undesirably develop an internal pressure in an aqueous environment.

In contrast, osmotic pressure causes some rigidity in the devices of Laughlin, which can aid in their retention in the vagina. However, development of internal hydrostatic pressure due to osmotic effects can cause at least two disadvantages in the Laughlin devices: (1) this pressure stresses the membrane structural components of the device making them more prone to rupture under the influence of more external force than they would be otherwise; and (2) this pressure precludes the use of products having relatively broad unsupported membrane areas in the present vaginal contraceptive application. Products so designed would undesirably inflate to uncomfortable and potentially contraceptively ineffective shapes. In any case, osmotic pressure is not, per se, the force which moves surfactant out of either the Laughlin devices or the devices disclosed herein. Rather, in both cases, it is the trans-membrane chemical potential (i.e., substantially the surfactant monomer concentration) difference which causes release of spermicidal surfactant monomers from the device. However, as noted above, Laughlin employs microporous membranes, such as swollen cellulose, which comprise microporous, water-filled channels through which the monomers are transported. In contrast, the present devices use non-porous membrane materials through which the surfactant monomers migrate by first dissolving therein then diffusing therethrough.

Moreover, the devices herein do not operate by an osmotic pressure mechanism and are thus entirely different from that of art-disclosed, osmotically-actuated "pump" devices for delivering drugs.

Highly preferred devices are those operating by a controlled release mechanism. However, devices operating by a sustained release mechanism can also be constructed in the manner disclosed herein so that they can be retained in the vagina during intercourse. Accordingly, sustained release devices of the unique construction and shape of the devices herein are fully contemplated by this invention.

CONTAINER

Broadly, the present devices comprise a container, or multiple containers, said container being insoluble in vaginal fluids, in a total device of the configuration described hereinabove. The container has the surfactant solution enclosed therein. At least one portion of the container comprises a non-porous polymeric membrane which permits the release of surfactant monomers into the vagina, but which substantially prevents the transport of the larger surfactant micelles. In short, the membrane is the transport surface which selectively discriminates between passage of monomers and micelles.

Containers used in the present devices can be partly made of any stable material such as glass, plastic, etc., which is not permeable, even to surfactant monomers. Of course, the containers should be made from a material which is inert to the surfactant solutions being used, as well as to the vaginal tissues, but selection of inert container materials is not a problem. At least some portion of the container used in the present devices must comprise a non-microporous polymeric membrane which allows diffusion of the spermicidal surfactant monomers therethrough and into the vaginal cavity. For the reasons disclosed above, at least that wall of the container which faces the cervical os comprises the controlled release membrane. Alternatively, the entire device can be made of the membrane material.

Preferred controlled release devices are those wherein the container comprises a dome-shaped envelope of the controlled release membrane.

The membranes used in the controlled release devices are characterized by parameters which reflect their strength, integrity and ability to pass surfactant monomers and to retain surfactant micelles, as follows.

The membranes should be substantially water-insoluble so that they maintain their strength and integrity when in contact with body fluids.

Since the devices are to be used in contact with body fluids and tissues, the membranes (and total container and device) should be toxicologically acceptable. Moreover, the membrane material will most preferably be immunologically acceptable and will not be rejected by the body's natural defense mechanism nor have any untoward effect on the rate of antibody formation, and the like.

The membrane must possess the ability to provide metered release of the surfactant monomers in order to provide the prolonged contraceptive benefit of the article.

The membrane must be sufficiently strong, yet flexible, so that it can be fashioned into the highly preferred shape of the devices disclosed herein.

The membranes employed herein comprise non-porous elastomers, preferably silicone polymers of latex rubbers, either natural or synthetic. The membranes generally have a thickness in the range of from about 0.02 mm to about 0.6 mm, preferably about 0.1 mm to about 0.4 mm. By selecting a membrane thickness within this range, stable, non-fragile, yet flexible and comfortable articles which effectively transport surfactant monomers to the vagina are provided.

The silicone polymers used in preparing the membranes for use in the present devices are preferably polydimethylsiloxanes, i.e., silicone polymers which contain the repeating unit.

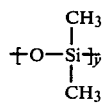

wherein y is an integer in the range of about 100–100,000.

Repeating units of the silicone polymer can contain side-chain branching and cross-linking, e.g.,

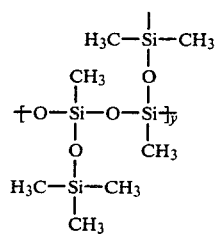

Various functional groups may be present in the basic silicone polymer structure to facilitate cross-linking-/curing.

Silicone polymers suitable for use herein can be prepared, for example, by hydrolyzing dimethyldichlorosilane or mixtures of dimethyldichlorosilane, trichloromethylsilane and chlorotrimethylsilane with water, in well-known fashion. Alternatively, siloxane "oligomers" can be polymerized and "cured" in various ways well known in the art. Silicone polymers suitable for preparing the mebranes for use in the present invention are also available, commercially, from suppliers such as the Dow Corning Corporation and the General Electric Corporation.

The latex rubbers which can be used in the present invention can be either the natural or synthetic latex rubber polymers which are commercially available. Such materials include, for example, the neoprene-type rubbers, the Buna ®-type rubbers, and the like. Natural or synthetic rubber which is calendered or molded can also be used.

Other types of non-porous polymers which can be used to fashion membranes for use with devices of the present type comprise, for example, mixtures of silicone polymers and latex rubbers; copolymers of silicone polymers and various other polymeric materials such as the polycarbonates, and the like; elastomers such as the well-known styrene/butadiene block copolymers; ethylene-vinyl acetate copolymers, etc.

Various polymeric membranes suitable for use in the contraceptive devices of the present invention can be determined easily using the surfactant Transport Procedure, disclosed hereinafter.

Highly preferred membranes for use herein are the non-porous membranes comprising silicone polymers, especially the polydimethylsiloxanes manufactured under "clean" conditions and marketed for various medical uses. Such materials are safe for prolonged use in contact with human tissues and provide excellent transport of surfactant monomers, especially the preferred, nonionic spermicidal surfactants of the type $C_{10}EO_5$ and $C_{10}EO_6$, as described hereinafter. These silicone polymers can readily be fashioned into membranes for use in devices having the preferred dome-shaped configuration disclosed herein. Typical examples of such silicone materials include Silastic ®382 and Dow Corning ® MDX 4-4210, MDX 4-4515, MDX 4-4516 and Q 7-2213, available from the Dow Corning Corporation.

SPERMICIDAL SURFACTANT

The use of micelle-forming surfactant solutions in the present contraceptive devices results in several important advantages over other types of metered dosage systems.

First, the surfactants employed as the active agent of the contraceptive devices of the present invention appear to function by an entirely localized effect on motile sperm. (The terms "spermicide" and "spermicidal" as employed herein encompasses surfactants which truly "kill" animal, including human, sperm as well as those which immobilizes or otherwise render sperm cells inactive.) Accordingly, undesirable side-effects which can accompany the prolonged use of systemic contraceptive drugs such as hormones are avoided.

Moreover, the use of safe, effective surfactants as the spermicide permits the formulator of the present devices to employ a large excess of the spermicide therewith. The controlled release feature allows formulation of devices containing more spermicide (surfactant) than the usual expected need but (1) reduces the probability of side-effects by regulating the concentration to a minimum level, and (2) allows for unusual variations in the amount of spermicide required or in the time period over which it might be needed. Accordingly, a "safety factor" of the order of several-fold vis-a-vis prolonged contraceptive efficacy is provided by the present devices.

The devices herein can be somewhat flaccid, rather than turgid. Accordingly, the pressure differential across the enclosing container is small, or zero, and the container is stable and is not subject to hydrostatic rupture. This desirable attribute of the present devices is to be contrasted with the situation which occurs when a similarly concentrated solution of a non-micelle-forming solute of similar molecular weight is enclosed by a water-permeable diffusion membrane, whereupon internal hydrostatic pressures of tens or hundreds of atmospheres can be developed due to osmotic effects, thereby leading to rupture of the membrane.

The surfactants employed in the present devices and processes are characterized by several parameters. In general, the surfactants are selected from those which, in combination with the semi-permeable membrane described hereinabove, provide an appropriate relationship between release and the desired contraceptive end use of the devices.

The surfactants herein are characterized by their ability to dissolve in a solvent (normally, water) and to form an association colloid, or micelles, therein. It has now been discovered that the surfactant micelles do not penetrate the wall of the membranous containers used herein. However, surfactant monomers do diffuse through the membranous walls and into the vagina. Thus, by virtue of the equilibrium between micellar and monomeric surfactant, the solution of surfactant, micelles provides a reservoir for the controlled delivery of spermicidal surfactant monomers to the environment external to the device, i.e., the vagina, expecially the area immediately around the cervical os. In a surfactant solution which is sufficiently concentrated to form true micelles, the concentration of monomer in equilibrium with the micellar surfactant remains substantially constant at the so-called "critical micelle concentration" (cmc) over a wide range of total surfactant concentration. In order to realize fully the unique advantages of surfactants in devices of the present type, it is preferred to use those spermicidal surfactants having a cmc of at most about $5 + 10^{-3}$ Molar (M). In particular, by choosing surfactants with this low cmc, the user of the present devices is exposed to only minimum amounts of surfactants, thereby minimizing any possible toxicological hazards.

It is to be appreciated that "neat" surfactants, i.e., not in solution, are not in the form of micellaraggregates and, accordingly, simply pass through the walls of the membranes in an undesirable, uncontrolled manner, thereby eliminating the reservoir effect provided by surfactant micelles.

When used as between-period contraceptives, it is, or course, necessary to select surfactants which produce the desired spermicidal response. Moreover, to secure the benefits of controlled release, it is necessary also to select surfactants whose monomers are rapidly transported through the membranous walls of the container to establish an effective concentration of surfactant in the vaginal area.

From the foregoing considerations it will be appreciated that various surfactants can be tested in vitro in a simple medium which approximates various body fluids (such as physiological saline or distilled water) to determine the concentration at which the surfactant must be present in such medium to provide spermicidal efficacy. Surfactants whose monomers are transported through the enclosing membrane of the device to provide at least the aforesaid effective concentration in the medium are useful herein. Upon immersion in an external solvent (e.g., vaginal fluids) the controlled release devices herein deliver surfactant monomers to the external solvent in the rapid, or "primary", transport process. After this external concentration reaches, approximately, the cmc of the surfactant, monomer transport slows drastically, since monomer concentration on both sides of the semi-permeable membrane is nearly equal. Slower, "secondary" transport processes may carry a bit more of the surfactant through the membrane to the vagina, but this does not substantially deplete the surfactant reservoir in the present devices.

From the foregoing, it follows that, for the desired spermicidal effect to be realized, the ratio, R, of the cmc of the surfactant to its spermicidally-effective concentration, $C_{sperm.}$, e.g., in saline, i.e., $$R = cmc/c_{sperm.}$$

should be greater than or equal to about 1. Similar considerations hold for external media other than saline, i.e., fluid media such as vaginal fluids, water, etc., in which the present surfactant monomers are soluble. Accordingly, the preferred compounds for use in the devices described herein have values of R which are greater than or equal to ca. 1, i.e., $$R \geq ca. \ 1.$$

A variety of surfactants exhibit a cmc less than about $5 \times 10^{-3}$ M and meet this criteria for use in the preferred controlled release devices herein. Several surfactant types having this preferred cmc provide a desirable spermicidal response. Moreover, several surfactants exhibit the requisite relationship, $R \geq ca. \ 1$, between cmc and spermicidal activity.

Based solely on the foregoing considerations, representative examples of surfactants useful herein include nonionic surfactants such as n-$C_{10}H_{21}(OCH_2CH_2)_5OH$ (abb. $C_{10}EO_5$) and n-$C_{10}H_{21}(OCH_2CH_2)_6OH$ ($C_{10}EO_6$); semipolar surfactants such as $C_{12}H_{25}S(NH)_2CH_3$ and $C_{12}H_{25}(CH_3)_2AsO$; and cationic surfactants such as $C_{16}H_{33}N^+(CH_3)_3,Cl^-$ and $C_{16}H_{33}N^+C_5H_5,Cl^-$. These surfactants are characterized by $R \geq 2$ and cmc $< 10^{-3}$M.

It is to be understood that other surfactants having a cmc of about $10^{-3}$ M, or less, but which exhibit somewhat lower activity as spermicidal agents, i.e., surfactants wherein ca. $1 > R > 2$, can be employed in controlled release articles. However, the biological response to these latter surfactants is somewhat less than that of the preferred group, and the efficacy margin, i.e., R-1, is not as great. Included among this group of surfactants are n-$C_{12}EO_9$; n-$C_{16}EO_1SO_4^-$,Na$^+$; $C_{12}H_{25}(CH_3)_2PO$; n-$C_{10}EO_4$; $C_{12}H_{25}(C_2H_5)_2PO$; $C_{16}H_{33}$ammoniopropanesulfonate; and nonylphenol nonaethoxylate.

As can be seen from the foregoing, various surfactant types are useful in controlled release contraceptive devices of the present type. However, when devices designed for use as between-period contraceptives in humans are being prepared, additional physio-chemical properties of the surfactants must be considered. For example, the surfactants should be toxicologically acceptable for use in the body over extended time periods. The surfactants should also be non-irritating to the delicate tissues of the vagina and uterus. The preferred surfactants should not substantially bind serum proteins found in the vaginal area between periods of menstrual flow, inasmuch as the bound surfactant-protein moiety does not function as a spermicide and accelerates the depletion of surfactant from the reservoir (micelles) within the device. The surfactant monomers must be able to dissolve or partition into the enclosing membrane of the device and diffuse through the membrane in an efficient and effective manner. Finally, the surfactant should be selected from those which do not bind to charged sites in the enclosing diffusion membrane, since binding inhibits the passage of the surfactant monomers through the membrane. In particular, ionic surfactants are troublesome in this regard. Moreover, some ionic surfactants are too polar to partition into and diffuse through the preferred silicone membranes efficiently.

Based on the foregoing factors, and considering the high spermicidal activity of the compounds, the alkylene oxide nonionic surfactants, especially the well-known condensation products of ethylene oxide with aliphatic alcohols or alkyl phenols, are preferred for use herein. In particular, $C_{10}EO_5$ and $C_{10}EO_6$ surfactants are most preferred for use in the present controlled release contraceptive devices. As between these latter compounds, $C_{10}EO_5$ has the advantage of the lower molecular weight, and therefore provides more spermicidal monomer per given weight of compound. Accordingly, $C_{10}EO_5$ is most preferred for use in the between-period, controlled release contraceptive devices of this invention.

The surfactants disclosed hereinabove are all well known from the detergency arts and can be made by various art-disclosed processes.

SURFACTANT TRANSPORT PROCEDURE

A cell for testing transport of surfactant monomers through membranes is as follows. A 40 mm (diameter)×50 mm (length) poly-methylmethacrylate rod is halved and each half is suitably machined to provide cavities 16 mm (diameter)×10 mm (depth), such that the cavities abut when the rod halves are reassembled. Each cavity is provided with two inlet holes for filling and sampling. A brass clamp is used to hold the two cell halves firmly together.

The surfactant transport testing is carried out in the following manner. A disc 3 cm in diameter of the membrane material to be tested is sandwiched between the cell halves, enclosing a 3 mm glass bead on each side of the membrane to provide stirring. One half of the cell is filled with distilled water and the other half is filled with an aqueous solution of a radiolabeled surfactant. The inlet holes are sealed with waterproof tape and the cell is placed in a 37° C. bath in a device which allows the cell to be rotated axially at approximately 50 rpm. Periodically, the cell is raised from the bath and the solution in the desired compartment sampled.

A typical procedure using a membrane of polydimethylsiloxane (Dow Corning ® MDX 4-4210) is as follows. After charging the cell, the cell is maintained in the 37° C. bath for varying time periods, after each of which the tape is removed from the inlet holes and duplicate 10 microliter (μl) samples are removed by syringe and expressed into a counting vial. In the subsequent scintillation counting, each sample vial is charged with 10 μl of a solution of 0.8% 2-diphenyloxazole and 0.01% of 1,4-bis-[2-(4-methyl-5-phenyloxazolyl)]-benzene in a 1:1 ethanol/toluene mixture. The vials (two for each time period) are then placed in the refrigerator compartment of a counting instrument and cooled to 4° C. before being counted for 5 minutes each. The counts per minute are converted to ppm by applying a factor found by counting one or more standard samples. By taking samples at regular intervals, a curve plotting the surfactant concentration in the initially surfactant-free side of the cell versus the time of sampling can be drawn which describes the transport of the surfactant across the membrane.

Following the Surfactant Transport Procedure set forth hereinabove, the cell cavity designated (A) is charged with surfactant solution and the cavity designated (B) is charged with distilled water. The cell cavities are separated by the test membrane, e.g., polydimethylsiloxane. The concentration of surfactant transported to cavity (B) is determined in the foregoing manner, and the graph of the concentration of surfactant in (B) versus time is plotted.

This graph describes a monomer transport curve which at the outset rises at a high rate (primary slope) and beyond a certain time rises at a much lower rate (secondary slope). The monomer transport curve has the general form $C = C_2(1 - e^{-t/\tau}) + S_2 t$, where C=surfactant concentration in cavity (B), $C_2$=the zero time intercept of the secondary slope, t=time, $\tau$=the time constant, and $S_2$=the secondary slope. The primary slope, $S_1$, is the slope of the curve at t=0 and is given by $$S_1 = C_2/\tau + S_2.$$

For controlled release devices of the present type, the combination of surfactant and a suitable membrane should yield a monomer transport curve wherein $S_1$ is relatively large, $S_2$ is relatively small, and $C_2$ is about equal to the cmc of the surfactant being tested. The ratio of $S_2/S_1$ is from 0 to about 0.1. $S_1$ should generally be no less than about 10 ppm/hr. and preferably will be in the range of about 100 ppm/hr. to about 200 ppm/hr.

Based on the foregoing, surfactant/membrane combinations can be selected which will provide controlled release articles of the present type. A highly preferred article herein which is particularly useful as a vaginal contraceptive comprises from about a 5% to about a 50% (wt.) aqueous solution of $C_{10}EO_5$ enclosed within a polydimethylsiloxane membrane.

METHOD OF MANUFACTURE

The following describes a typical method of manufacturing a preferred, double-domed article of the type disclosed herein. While the description relates to a preferred and convenient process for preparing the articles from a silicone polymer, various methods of manufacture can be employed to prepare other devices encompassed by the present invention.

Dow Corning ® MDX 4-4210 Clean Grade Elastomer (Dow Corning Corporation, Midland, Mich.) is supplied in two parts: an elastomer base and a curing agent which, when mixed and cured, form the finished silicone polymer membrane. In practice, about 10 parts of elastomer base are mixed with about 1 part of curing agent. The mixture is deaerated in a vacuum chamber until no more entrapped air can be seen. The deaerated mixture is then injected into mold cavities of appropriate dimensions for the halves of the dome-shaped device. The silicone halves are cured by heating in the mold at ca. 125° C. for at least about 15 minutes. It will be appreciated that the mold dimensions can be adjusted to provide the desired thickness of the resulting silicone membrane.

The choice of curing agent for silicone polymers is not critical to the operation of the devices prepared in the manner of this invention. Depending on the particular silicone polymer chosen, various platinum-based, tin-based and peroxide-based catalysts or curing agents for silicones well known in the art are suitable for use in preparing silicone membranes. However, it has now been discovered that, in prolonged use in the vagina, some curing agents can cause the silicone membrane to become discolored. While this discoloration does not deleteriously affect the operation of the devices, they are rendered unsanitary in appearance. Apparently, some naturally-occurring sulfur and/or amino compounds present in vaginal fluids somehow interact with tin-based curing agents such as stannous octoate to cause the discoloration. Whatever the cause, it is preferable, from an aesthetic standpoint, to avoid the use of tin-based curing agents and curing agents which form colored complexes with the components of vaginal fluids in the preparation of optimized particles of the present type. Accordingly, peroxide-based or, preferably, platinum-based silicone curing agents are preferred for use herein. Such materials are well known in the art and can be selected from listings in standard texts. Alternatively, suitable polymers substantially free from color-forming curing agents can be selected by preparing and curing silicone polymers in standard fashion and incubating the polymers in the vaginas of live laboratory animals to determine their propensity for discoloration.

After having prepared the two halves of the double dome-shaped device, a uniform layer of silicone adhesive (e.g., Silastic ® Medical Adhesive Silicone Type A, Dow Corning Corporation), is placed around the periphery of the upper half of the dome. The upper half and lower half are joined and pressed to squeeze out any excess adhesive from the seal area. The excess adhesive is removed and the adhesive which seals the double dome-shaped device is allowed to cure for 24 hours, or longer.

An aqueous solution of the spermicidal surfactant is prepared. The solution is taken up in a syringe fitted with a 25 gauge needle. The surfactant solution is injected into the free space within the double dome-shaped device through the peripheral rim. With the needle still in place, any air remaining inside the device is removed. (Needle holes from this procedure do not leak with pressures encountered in use.)

In an alternative filling procedure, the upper dome half of the device is positioned downwardly, the surfactant solution is poured into this half, and the bottom dome half of the device is sealed thereto while in a downward position.

After filling, the sealed device is placed in a vial and covered with approximately 50 mls of water. The vial is loosely covered and placed in an autoclave at 15 psig (121° C.) for 30 minutes. After cooling, the autoclave is opened and the closure on the vial is tightened to provide individually packaged, sterile contraceptive devices suitable for distribution to users.

The following examples illustrate the practice of this invention, but are not intended to be limiting thereof.

EXAMPLE I

A device of the type depicted in FIG. 2 is prepared from Dow Corning ® MDX 4-4210 Clean Grade Elastomer using the methods described hereinabove. The device is in the form of a disc having a double dome of the silicone membrane. The thickness of the membrane is ca. 0.25±0.15 mm. The base of the device has an outside diameter of ca. 55±10 mm and an inside diameter of ca. 50±15 mm. The height of the upper membrane of the double dome from the base of the device is ca. 25±5 mm, whereas the height of the lower membrane of the double dome from the base of the device is ca. 18±5 mm, whereby the total volume of the dome-shaped container resulting from sealing the edges of the device is ca. 5 cc.

A device of the foregoing type is substantially filled with a 25% (wt.) aqueous solution of the $C_{10}EO_5$ surfactant. Excess air is removed. The device is autoclaved and is ready for use as a vaginal contraceptive.

The device is placed in the vagina posterior to the introitus in a manner such that the concavity of the dome substantially covers and "caps" the cervical os. The device is worn during the time between menses and safely and continuously delivers a spermicidally effective amount of $C_{10}EO_5$ surfactant to the vaginal area. In particular, the positioning and shape of the device bathes the cervical os with the spermicidal surfactant. The device is quite comfortable and remains in place during intercourse.

In the device of Example I, the $C_{10}EO_5$ surfactant is replaced by an equivalent amount of $C_{10}EO_6$ surfactant and excellent spermicidal results are secured.

EXAMPLE II

A device of the configuration depicted in FIG. 2 is prepared as follows. The internal portion of the device (i.e., the portion to be placed in close proximity to the cervical os) is prepared from Dow Corning ® MDX 4-4210 Clean Grade Elastomer using the methods described in Example I. The thickness of the silicone membrane is ca. 0.25±0.15 mm.

The other half of the device is prepared from a substantially non-permeable, polyethylene terephthalate (PET) plastic having a thickness of ca. 0.6±0.1 mm.

The two halves are assembled in the manner described above to provide a "double-domed" shaped device. The inner concavity of the device comprises the semi-permeable silicone membrane. The base of the device has an outside diameter of ca. 55±10 mm and an inside diameter of ca. 50±15 mm. The height of the outer PET halt portion of the double dome from the base of the device is ca. 25±5 mm, whereas the height of the inner, silicone membrane of the double dome from the base of the device is ca. 18±5 mm, whereby the total volume of the dome-shaped container resulting from sealing the edges of the device is ca. 5 cc.

A device of the foregoing type is substantially filled with a 25% (wt.) aqueous solution of the $C_{10}EO_5$ surfactant. Excess air is removed. The device is autoclaved and is ready for use as a vaginal contraceptive.

The device is placed in the vagina posterior to the introitus in a manner such that the concavity of the dome substantially covers and "caps" the cervical os. The device is worn during the time between menses and safely and effectively delivers a spermicidal amount of $C_{10}EO_5$ surfactant to the vaginal area. In particular, the positioning and shape of the device bathes the cervical os with the spermicidal surfactant via the inner silicone membrane. Substantially none of the surfactant migrates through the PET outer dome into the general vaginal cavity. Thus, substantially all of the surfactant is delivered to the intended situs, i.e., the cervical os and immediate surrounding area. The device is quite comfortable and remains in place during intercourse.

In the device of Example II, the $C_{10}EO_5$ surfactant is replaced by an equivalent amount of $C_{10}EO_6$ surfactant and excellent spermicidal results are secured.

EXAMPLE III

A flat, disc-shaped silicone device is prepared in the manner described hereinabove by appropriate selection of die configuration. The device has the general dimensions of the device of Example I, with the exception that the container formed by the membranes is flat, frather than domed.

The disc-shaped device is substantially filled with a 50% (wt.) aqueous solution of the $C_{10}EO_5$ spermicidal surfactant. Excess air is removed. The device is autoclaved in the manner described hereinabove and is ready for use as a vaginal contraceptive.

The device is placed in the vagina posterior to the introitus and in a manner such that the central portion of the disc (which comprises the membranous container) is in the closest possible proximity to the cervical os. The device is worn during the time between menses and safely and effectively delivers the spermicidal surfactant to the vaginal area during that time. The device is quite comfortable and remains in place during intercourse.

The device of Example III is prepared using synthetic rubber and excellent spermicidal results are secured.

The device of Example III is prepared from the following polymeric materials: polycarbonate; styrene butadiene block copolymers; and ethylene-vinylacetate copolymers, said polymeric materials being used in combination with both $C_{10}EO_5$ and $C_{10}EO_6$. Excellent spermicidal results are secured.

EXAMPLE IV

A device of the general double-domed disc configuration depicted in the Figures is prepared as follows.

The inner dome which comprises the 0.25 mm thick membranous transport surface is prepared from Dow Corning ® MDX 4-4210 Clean Grade Elastomer using the methods described hereinabove.

The outer dome disc is prepared from non-permeable PET plastic having a thickness of ca. 0.55 mm.

The inner and outer discs are sealed together around their peripheral edges, but without forming a retaining rim. The domed configuration is maintained by virtue of the dimensional stability of the relatively thick, resilient, yet comfortable outer PET dome.

A device of the foregoing type having the approximate dimensions of the article of Example I provides a dome-shaped container having a volume of ca. 5 cc.

A device of the foregoing type substantially filled with ca. 30% (wt.) aqueous solution of $C_{10}EO_5$ surfactant is used as a vaginal contraceptive. The device is placed in the vagina posterior to the introitus in a manner such that the concavity of the dome, i.e., the inner, silicone membrane, substantially covers and "caps" the cervical os. The device is worn during the time between menses and safely and continuously delivers a spermicidally effective amount of $C_{10}EO_5$ surfactant to the vaginal area. In particular, the positioning and shape of the device bathes the cervical os with the spermicidal surfactant. The device is quite comfortable and remains in place during intercourse.

What is claimed is:

1. A contraceptive device especially adapted for use within the vaginal cavity at a position posterior to the introitus and with a face in close proximity to the cervical os, characterized by: vaginal retaining means having affixed thereto one or more container having walls, at least a portion of the walls comprising a substantially non-porous, semi-permeable membrane, said containers holding a reservoir of spermicide comprising an aqueous solution of a micelle-forming spermicidal surfactant compound at a concentration at or above the critical micelle concentration of said surfactant compound, said membrane-walled containers being maintained in position in the device by positioning means, thereby providing a transport surface on the face of the device.

2. A device according to claim 1 wherein the transport surface extends substantially across the face of the device.

3. A device according to claim 1 which is disc-shaped.

4. A device according to claim 3 wherein the transport surface extends substantially across the face of the device.

5. A device according to claim 1 which is domed, whereby the device can be positioned is substantially cap the cervical os.

6. A device according to claim 3 which is a dome-shaped disc.

7. A device according to claim 6 wherein the transport surface extends substantially across the face of the device.

8. A device according to claim 1 wherein only the container walls which face the cervical os comprise the substantially non-porous, semi-permeable membrane transport surface.

9. A device according to claim 8 wherein the membrane has a thickness in the range of from about 0.02 mm to about 0.6 mm.

10. A device according to claim 1 wherein all container walls comprise the substantially non-porous, semi-permeable membrane transport surface.

11. A device according to claim 10 wherein the membrane has a thickness in the range of from about 0.02 mm to about 0.6 mm.

12. A device according to claim 1 wherein the semi-permeable membrane comprises a pharmaceutically-acceptable silicone polymer.

13. A device according to claim 12 wherein the silicone polymer is substantially free from color-forming curing agents.

14. A device according to claim 1 wherein the spermicidal surfactant compound is a nonionic surfactant selected from ethylene oxide condensates of aliphatic alcohols and ethylene oxide condensates of alkyl phenols.

15. A device according to claim 14 wherein the surfactant compound is characterized by a critical micelle concentration of at most about $5 \times 10^{-3}$ Molar.

16. A device according to claim 15 wherein the surfactant compound is $C_{10}EO_5$, $C_{10}EO_6$, or mixtures thereof.

17. A contraceptive device according to claim 1, comprising: a double-walled, dome-shaped disc suitable for capping the cervical os, at least one wall of said disc comprising a non-porous, semi-permeable membrane transport surface having a thickness in the range of from about 0.1 mm to about 0.4 mm, said walls being sealed together to provide containers, said containers holding an aqueous solution comprising from about 10% to about 50% by weight of $C_{10}EO_5$ or $C_{10}EO_6$.

18. A device according to claim 17 wherein the membrane is a silicone polymer.

19. A device according to claim 18 wherein the silicone polymer is substantially free from color-forming curing agents.

20. A device according to claim 14 wherein the walls are sealed together around their peripheral edges to provide retaining means comprising a dimensionally-stable rim.

21. A device according to claim 20 wherein only the transport surface facing the cervical os comprises the semi-permeable membrane.

22. A device according to claim 21 wherein the membrane is a silicone polymer which is substantially free from color-forming curing agents.

23. A device according to claim 20 wherein the membrane is rubber.

24. A dome-shaped device according to claim 17 wherein the outer dome-shaped wall comprises a dimensionally-stable, non-permeable retaining means and wherein the inner wall comprises the non-porous, semi-permeable membrane transport surface.

25. A device according to claim 24 wherein the membrane is a silicone polymer which is substantially free from color-forming curing agents.

26. A device according to claim 24 wherein the membrane is rubber.

27. A method for achieving contraception in the vagina, comprising: inserting within the vaginal cavity at a position posterior to the introitus and with a face in close proximity to the cervical os a device characterized by:

vaginal retaining means having affixed thereto one or more containers having walls, at least a portion of the walls comprising a substantially non-porous, semi-permeable membrane, said containers holding a reservoir of spermicide comprising an aqueous solution of a micelle-forming spermicidal surfactant compound at a concentration at or above the critical micelle concentration of said surfactant compound, said membrane-walled containers being maintained in position in the device by positioning means, thereby providing a transport surface on the face of the device, and placing the device so that the transport surface substantially covers the cervical os, whereby surfactant monomers diffuse from the device and substantialy bathe the cervical os to provide a spermicidal effect.

* * * * *